United States Patent
Wang et al.

(10) Patent No.: US 9,377,397 B2
(45) Date of Patent: Jun. 28, 2016

(54) CALIBRATION SYSTEM AND METHOD OF USING MID-IR LASER MEASURE AND MONITOR EXHAUST POLLUTANT

(75) Inventors: Yu Wang, North Wales, PA (US); William Howard Eberhardt, Cherry Hill, NJ (US); Mark Wayne Holt, Emmaus, PA (US); Jamison W. Janawitz, Overland Park, KS (US)

(73) Assignee: The Babcock & Wilcox Company, Barberton, OH (US)

( * ) Notice: Subject to any disclaimer, the term of this patent is extended or adjusted under 35 U.S.C. 154(b) by 1862 days.

(21) Appl. No.: 12/633,862

(22) Filed: Dec. 9, 2009

(65) Prior Publication Data

US 2011/0132063 A1   Jun. 9, 2011

(51) Int. Cl.
| | |
|---|---|
| G01N 21/93 | (2006.01) |
| G01N 21/3504 | (2014.01) |
| G01N 21/27 | (2006.01) |

(52) U.S. Cl.
CPC .......... *G01N 21/3504* (2013.01); *G01N 21/276* (2013.01)

(58) Field of Classification Search
USPC .............................................. 250/345.1, 343
See application file for complete search history.

(56) References Cited

U.S. PATENT DOCUMENTS

| | | | |
|---|---|---|---|
| 4,019,056 A | 4/1977 | Block et al. | |
| 4,410,992 A | 10/1983 | Javan | |
| 4,489,239 A | 12/1984 | Grant et al. | |
| 4,549,080 A * | 10/1985 | Baskins et al. | ................ 250/343 |
| 4,934,816 A | 6/1990 | Silver et al. | |
| 5,364,795 A | 11/1994 | Sausa | |
| 5,877,862 A | 3/1999 | Nelson et al. | |
| 6,154,277 A | 11/2000 | Snelling et al. | |
| 6,181,419 B1 | 1/2001 | Snelling et al. | |
| 6,809,820 B2 | 10/2004 | Snelling et al. | |
| 2002/0158202 A1* | 10/2002 | Webber et al. | ........... 250/339.13 |
| 2004/0074279 A1* | 4/2004 | Forrest | ............................ 73/1.06 |
| 2006/0133714 A1* | 6/2006 | Sappey et al. | ................... 385/13 |

* cited by examiner

*Primary Examiner* — David Porta
*Assistant Examiner* — Shun Lee
(74) *Attorney, Agent, or Firm* — Eric Marich

(57) ABSTRACT

A method is provided of calibrating a system that detects presence of a pollution component within exhaust gases proceeding along an exhaust passageway. A measurement cell of a probe is isolated by movement of either the entire probe or a shield within the probe from the exhaust gas to allow reference gas to be detected by a laser beam in the mid-infrared range in the measurement cell to calibrate the system. In another example, a laser source is placed on one side of an exhaust passageway and a detector is placed on the other side. A reference cell is provided that is used to receive reference gas and calibrate the system. In yet another example, the exhaust gas is extracted from the passageway and is measured in a reference cell. The reference cell is also filled with reference gas when it is desired to calibrate the system.

8 Claims, 7 Drawing Sheets

CALIBRATION SYSTEM AND METHOD OF USING MID-IR LASER MEASURE AND MONITOR EXHAUST POLLUTANT

FIELD OF THE INVENTION

The subject application relates generally to systems for detecting presence of a pollution component within exhaust gases and specifically relates to use of a laser.

BACKGROUND OF THE INVENTION

Emissions sources produce exhaust that may contain one or more pollutants. For certain circumstances, it may be beneficial to control pollutant that proceeds to the environment. In order to control pollutants, the amount of pollutant contained with exhaust gases proceeding is monitored.

In general, the conditions within or near an exhaust passageway may be adverse and/or harsh. For example, elevated temperatures may be present. As another example, the corrosive agents may be present in the exhaust gases.

BRIEF SUMMARY OF THE INVENTION

The following presents a simplified summary of the invention of the subject application in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect the present invention provides a method of calibrating a system that detects a presence of a pollution component within an exhaust gas within an exhaust passageway. The method includes the step of providing a probe with a measurement cell for in-situ measurement of the exhaust gas where the probe operates to detect the pollution component from the exhaust gas. The probe includes a laser that emits a beam in the mid-infrared range. Another step in the method includes isolating the measurement cell of the probe from the exhaust gas of the exhaust passageway and providing a source of a reference gas that is transported to the measurement cell. Another step in the method includes operating the laser of the probe with the beam directed to the measurement cell that includes the reference gas, such that the beam interacts with the reference gas. The method further provides receiving at a detector at least one laser beam constituent subsequent to the interaction of the beam with the reference gas and determining an accuracy and a calibration of the system from the one or more constituents of the reference gas.

In accordance with another aspect the present invention provides a method of calibrating a system that detects a presence of a pollution component of an exhaust gas within an exhaust passageway without withdrawing the exhaust gas from the system. The method includes providing a laser that emits a beam in the mid-infrared range from a first side of the exhaust passageway. The method further includes the step of providing a first detector on a second side of the exhaust passageway for receiving the beam during a measurement of the presence of the pollution component within the exhaust gas. Another step includes providing a closed coupled reference cell on the first side of the exhaust passageway that is configured to be filled with reference gas during a calibration of the system. A laser source is operated to interact the beam of the laser with the reference gas during the calibration of the system. The method further provides determining the accuracy and the calibration of the system from one or more laser constituents of the reference gas.

In accordance with another aspect the present invention provides a method of calibrating a system that detects a presence of a pollution component within an exhaust gas within an exhaust passageway wherein the exhaust passageway includes an exhaust extraction portion. The method includes transporting the exhaust gas from the exhaust extraction portion to a closed coupled reference cell located on a first side of the exhaust passageway. A laser is provided that emits a beam in the mid-infrared range from a first portion of the closed coupled reference cell for measuring the presence of the pollution component within the exhaust gas. The method further includes providing a detector on a second portion of the closed coupled reference cell for receiving the beam and filling the closed coupled reference cell with reference gas for calibrating the system. The method further includes operating the laser to interact with the reference gas, receiving at the detector within the closed coupled reference cell the laser beam subsequent to the interaction of the beam with the reference gas, and determining accuracy and calibration of the system from one or more constituents of the reference gas.

BRIEF DESCRIPTION OF THE DRAWINGS

The foregoing and other aspects of the present application will become apparent to those skilled in the art to which the present application relates upon reading the following description with reference to the accompanying drawings, in which.

DETAILED DESCRIPTION OF THE INVENTION

Figure 1:
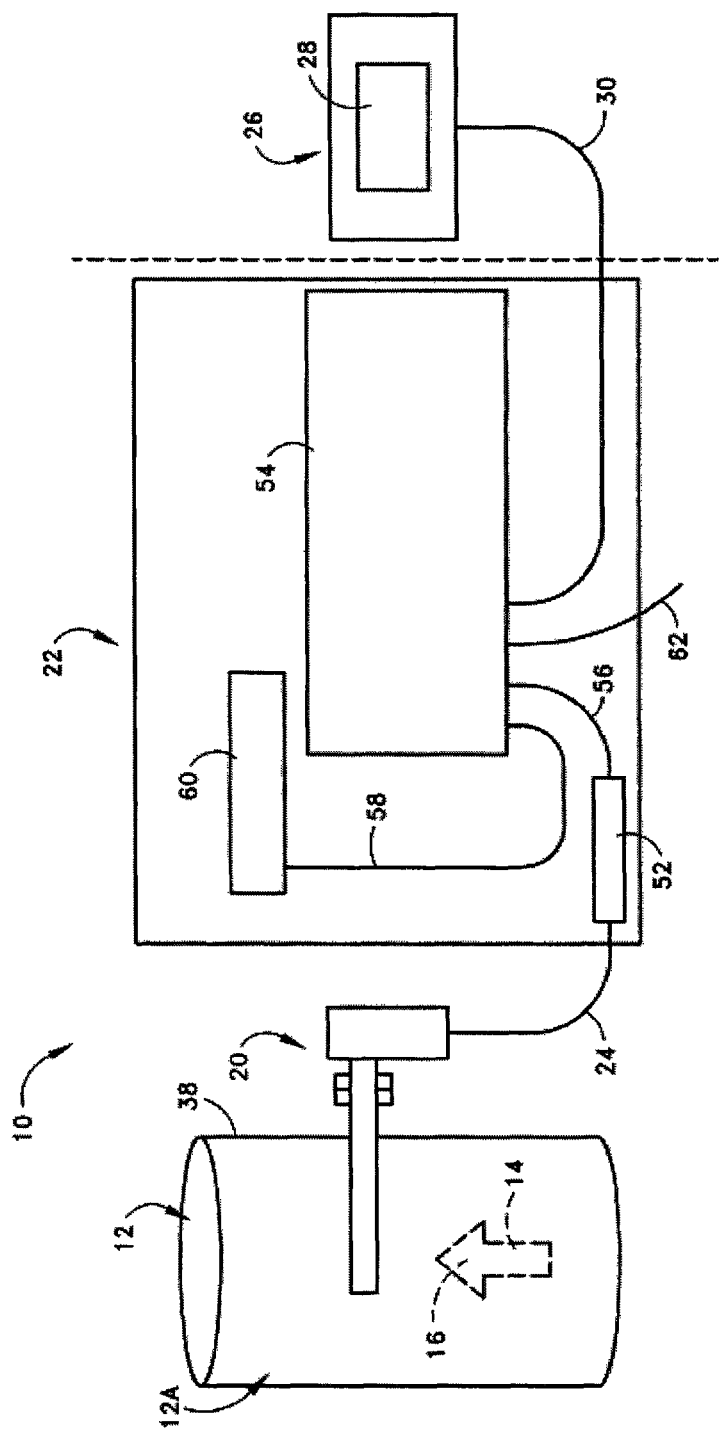
FIG. 1 is a schematic illustration of an example system associated with an exhaust passageway, with the system utilizing a method in accordance with the present invention.

Example embodiments that incorporate one or more aspects of the present invention of the subject application are described and illustrated in the drawings. These illustrated examples are not intended to be a limitation on the subject application. For example, one or more aspects of the subject application can be utilized in other embodiments and even other types of devices. Moreover, certain terminology is used herein for convenience only and is not to be taken as a limitation on the subject application. Still further, in the drawings, the same reference numerals are employed for designating the same elements.

Turning to the shown example of FIG. 1, an example system 10 in accordance with at least one aspect is shown. The system 10 is shown with an associated exhaust passageway 12. In the shown example, the exhaust passageway 12 includes a duct or an exhaust stack 12A (only partially shown and schematically shown). It is to be appreciated that the exhaust passageway 12 may include one or more components and/or structures that direct exhaust. Such components and/or structures may include portions of a combustion chamber, such as a combustion chamber of a boiler, and/or components/structures that are located intermediate the combustion chamber and the stack 12A. Also, the exhaust passageway may include a portion for extraction. These components/structures, including a possible portion for extraction, are collectively and individually represented by the exhaust passageway 12, with the phrase "exhaust passageway" to collectively or individually refer to the components/structures, including the possible portion for extraction.

Turning to the shown example, the exhaust passageway 12 is associated with an industry. The industry may be any of a variety of industries, such as manufacture processing or the like. The industry causes a creation of exhaust gases 14 (schematically represented by an arrowhead within the exhaust passageway 12) that proceed along (e.g., up in the shown example) the exhaust passageway. As will be appreciated, the conditions within the exhaust passageway 12 may be adverse. Examples of adverse conditions include excessive heat and/or corrosiveness.

It is possible that one or more pollutants 16 (schematically represented as merely a point within the gases 14) are present in the exhaust gases. Some example possible pollutants are NO, $NO_2$, CO, $CO_2$, $SO_2$, $NH_3$, $H_2S$, and $CH_4$. Of course, such listing of examples is not to be a limitation. Also, it is possible that some processing of the exhaust gases occurs along the exhaust passageway 12. Such processing may occur prior to the exhaust gases enter an exhaust stack 12A of the exhaust passageway 12, while the gases are proceeding along the stack and/or at/near exit of the exhaust stack. Examples of such processing include filtering, scrubbing, and after burner combustion. The processing of the exhaust gases may be for the purpose of limiting an amount pollutant(s) 16 that eventually proceed to the environment via the exhaust passageway 12.

Within the system 10, presence of a pollution component within the exhaust gases as indicative of at least one pollutant 16 is detected. It is to be appreciated that detection is to be broadly interpreted to include mere detection regardless of quantity and/or detection of quantity via any comparative measure. Examples of comparative measure include percentage of overall composition of exhaust gases, presence of measured amount above a threshold, and the like. Of course detection may also merely be determination of presence.

Turning to the shown example, the system 10 has a probe 20 that is located on the exhaust passageway 12 (e.g., in-situ in the stack of the passageway, but only by way of example), a probe controller 22 that is operatively connected 24 to the probe, and a programmable logic controller 26 with an operator interface terminal 28 that is operatively connected 30 to the probe controller. The probe controller 22 is located in relatively close proximity to the probe/exhaust passageway or alternatively at a remote location (e.g., such as a control room or a suitable shelter). Also, the programmable logic controller 26 is located at a suitable location. Examples of such suitable locations are a control room or other remote location, which is schematically represented by the dash dividing line within FIG. 1. Of course, these identified portions of the shown example are schematically presented and the person of ordinary skill in the art will appreciate that these portions may vary in construction and/or configuration within the scope of the present invention. Also, content of the system 10 may be varied to include other portions.

Figure 2:
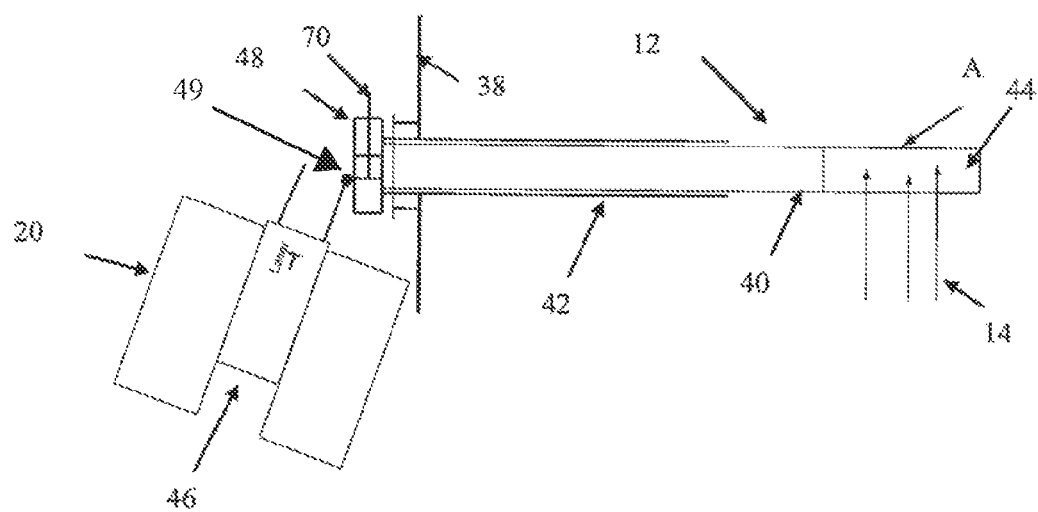
FIG. 2 is a schematic illustration of a probe of the example system shown in FIG. 1 and with a portion of the probe moved to allow access to the interior of the passageway and the probe portions therein for purposes of maintaining or adjusting the equipment.

Focusing first upon the probe 20 and its placement, attention is directed to FIG. 2. An aperture penetrates though a wall 38 (schematic line representation) of the exhaust passageway 12 from the exterior of the passageway to the interior of the passageway. The probe 20 has a guide path portion 40 that extends through the wall 38 and into the interior of the exhaust passageway 12. If the exhaust passageway includes a portion for extraction, the probe 20 and the associated wall 38 are configured in connection with the extraction as part of the exhaust passageway 12. The guide path portion 40 may be composed of any suitable construction and composition (e.g., a tube) to guide and/or shield laser light according to selected characteristics of the laser light utilized within the probe 20. For example, the guide path portion 40 may include a material that is a suitable medium for transmission of the laser light. It is worth noting that at least part of the guide path portion 40 of the probe 20 has direct exposure to exhaust gases. Thus, it is to be appreciated that at least part of the guide path portion 40 is subject to adverse conditions within the exhaust passageway 12. In one example, all or part of the probe 20 is shielded to limit particulate fouling. In particular, it is contemplated to shield a measurement cell cavity, thus reducing maintenance and facilitating long run times of instrument between cleanings. A fixed shield 42 can be provided to isolate the measurement cell or detection arrangement 48 from the exhaust gas.

Within the shown example, a schematic representation of the interaction between exhaust gases 14 and laser light is shown at the measurement cell 44 in an area A. It is to be appreciated that the interaction between (i.e., between the exhaust gases and the laser light) may result in specific absorption and/or transmission and/or reflection. As an example, absorption may be associated with the interaction with gaseous content of the exhaust gases. As another example, reflection may be associated with particulate matter carried within the exhaust gases.

At another portion of the probe 20, a laser source 46 is present. The laser source 46 generates and emits the laser light. It is to be appreciated that some amount of processing capability may be integrated and/or associated near the laser source 46. As discussed above, the laser light is directed into the interior of the exhaust passageway 12. In accordance with one aspect, the laser source 46 is a Quantum Cascade Laser (QCL). Such a QCL laser is operated to perform in the mid-infrared (mid-IR) range. An example of the mid-IR range within which the laser source 46 operates is within the frequency range of 4000 to 650 $cm^{-1}$. The laser source 46 may be operated in a continuous mode or in a pulsed mode. It is to be noted that the use of the QCL laser occurs at or near at least one adverse condition associated with the exhaust passageway 12. For example, the laser source 46 may be subjected to adverse heat levels. However, it is contemplated as one aspect of the present invention that the laser source 46 may be operated without any external cooling, such as a cryogenic cooling arrangement.

At yet another portion of the probe 20, a detection arrangement 48 is present. It is to be appreciated that some amount of processing capability may be integrated and/or associated near the detection arrangement 48. The detection arrangement 48 is for detecting interaction of the laser light with the exhaust gases 14. In one particular embodiment, the detection arrangement 48 is for detecting interaction with possible at least one pollutant 16 within the exhaust gases. Within the shown example, the detection arrangement 48 is for spectrometric measurement in the mid-IR range. Thus, the detection arrangement 48 receives at least one laser beam constituent (e.g., only certain spectral component) subsequent to the interaction of the beam with the gases. It is to be noted that the use of the detection arrangement 48 of the probe 20 occurs at or near at least one adverse condition associated with the exhaust pathway. For example, the detection arrangement 48 may be subjected to adverse heat levels.

In one example, the probe 20 is constructed and/or configured to withstand some level of adverse weather conditions. Such adverse weather conditions may include rain, snow or other precipitation/moisture. Also, such adverse weather conditions may include temperature extremes such as extreme heat or cold. Also, the laser source 46 is capable of moving (e.g., tilting) to permit access to portions of the probe 20 located within the exhaust passageway 12 as shown in FIG. 2. As one aspect, all or part (e.g., laser source 46) of the probe 20 has a modular designed to facilitate ease of maintenance and removal. For example, one portion, such as an electronics portion, may be designed with a movable design (e.g., a hinge) to allow electronics removal and repair without removing a connection flange and/or other probe components (e.g., a tube).

As stated, the probe 20 is operatively connected 24 to the probe controller 22. The connection 24 may include one or more lines for providing power to the probe, one of one lines to control operation of the laser source 46 of the probe (e.g., controlling continuous ON or pulsed ON), and one or more lines to receive signal(s) from the detection arrangement 48. The connection 24 may include one or more other lines, connections or conduits that extend between the probe 20 and the probe controller 22. The connection 24 may be via cable, fiber optic, and/or wireless. The detection arrangement 48 can also include a sliding bar 70 that is configured to open or block the communication of gases between the part of the probe 20 on the interior of the wall 38 and the part of the probe on the exterior of the wall 38.

In the shown example of the probe controller 22 in FIG. 1, a probe temperature controller 52 is provided. The function of the probe temperature controller 52 is to provide cooling to the probe 20. The cooling may take the form of transfer of cooling liquid to the probe 20. However, the inclusion of the probe temperature controller 52 may be optional. Also, it is possible that the probe temperature controller 52 is not operated.

Also within the probe controller 22 is an analytical system 54 operatively connected 56 within the probe controller 22. The connection 56 may be via cable, fiber optic, and/or wireless. The received signal(s) from the detection arrangement 48 are provided to the analytical system 54. Analysis of the data contained within the received signal(s) is performed within the analytical system 54. In one example, spectral analysis is performed. Specific spectral content may be present and/or absent. The presence and/or absence of specific spectral content can be indicative of presence of a pollutant 16 within the exhaust gases. Thus, the analytical system 54 can determine presence of the pollution component within emission gases using the data as provided by the received at least one laser beam constituent. The step of determining presence of the pollution component within emission gases may include determining a value indicative of the concentration of the component within the emission gases. In order to verify content, the analytical system 54 is operatively connected 58 to a gas verification unit 60 of the probe controller 22. The connection 58 may be via cable, fiber optic, and/or wireless.

As previously stated, the probe controller 22 is operatively connected 30 to the programmable logic controller 26 with the operator interface terminal 28. The connection 30 may be via cable, fiber optic, and/or wireless. The programmable logic controller 26 allows an operator to provide program control to the probe controller 22 and the system 10 as a whole. Also, the programmable logic controller 26 can be a data extraction location. The data may include pollution presence within the exhaust gases and may also include data about operation of the system. In addition or in the alternative, the probe controller 22 and/or the programmable logic controller 26 may be associated with a data conduit 62 that conveys data to another location (e.g., via a network). The data conduit 62 may be via cable, fiber optic, and/or wireless.

One aspect of the probe provides a method of detecting presence of a pollution component within exhaust gases within an exhaust passageway 12. The gases proceed along a path of the exhaust passageway 12 toward discharge. The method includes a step of providing a probe 20 that operates to detect the pollution component. In one specific example, the probe 20 includes a laser source 46 that emits a beam in the mid-infrared range. The probe 20 is placed within the exhaust passageway 12 directly within the path of the emission gases proceeding along the exhaust passageway 12. The laser source 46 of the probe 20 is operated with the beam directed to portion of the exhaust passageway 12 thought which the gas is proceeding along the path to discharge, such that the beam interacts with the gases and the possible component located therein. At least one laser beam constituent is received subsequent to the interaction of the beam with the gases. Presence of the pollution component within emission gases is determined using the received at least one laser beam constituent.

As another aspect, methodology may include the use of a probe 20 that includes a quantum cascade laser as the laser source 46. The laser source 46 may operate in the mid-infrared range. Thus, the provided laser source may be altered and the laser source can operate in a pulsed more or in a continuous mode.

Also, in one example, the probe 20, the components thereof, and/or the entire system 10 may be arranged to be subject to a calibration function. As one specific example, the probe 20 is calibrated in-situ (e.g., in stack). An in-situ calibration audit cell can be used for calibration across a large stream of gases. The audit cell could have a cell with a fixed length filled with a high concentration reference gas proportioned to the gas concentration. The probe output and/or the entire operation of the system could be monitored for provision of expected data.

Figure 3:
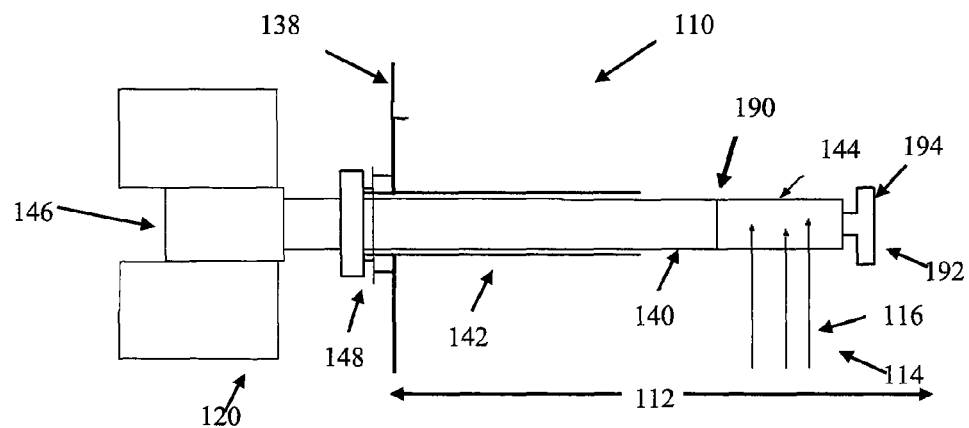
FIG. 3 is a schematic illustration of a system for measuring a pollution component of an exhaust gas and configured for conducting a calibration of the system where a probe is in a position for measuring and detecting the pollution in the exhaust gas.
Figure 4:
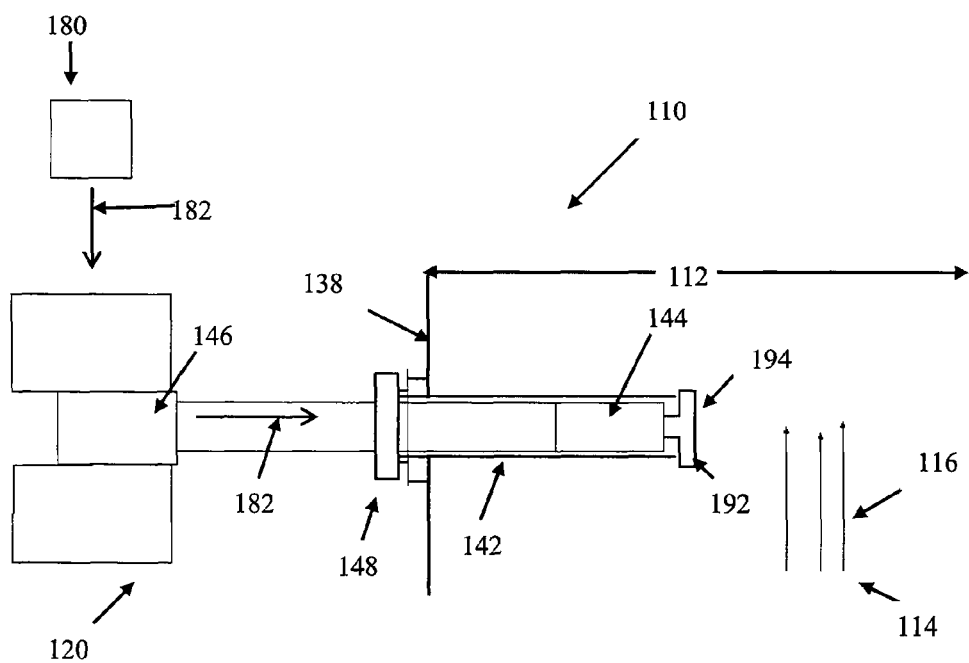
FIG. 4 is a schematic illustration of the system of FIG. 3 with the probe in a position where a measurement cell is isolated from the exhaust gas to allow calibration of the system to take place.

FIGS. 3, 4, 5, and 6 show a first example system 110 that is used to measure a pollution component of an exhaust gas 114 and is also configured for calibration of the system. The exhaust gas 114 can come from any source and can merely be a gas that a user wishes to measure the pollution of. As shown in FIG. 3, this example system 110 includes providing a probe 120 with a measurement cell 144 for measurement of the exhaust gas 114 wherein the probe 120 operates to detect the pollution component 116 from the exhaust gas 114, the probe 120 including a laser source 146 that emits a beam in the mid-infrared range. The next step in the method is to isolate the measurement cell 144 of the probe 120 from the exhaust passageway 112. As shown in FIG. 4, a source 180 of a reference gas 182 is provided and the reference gas 182 is transported to the measurement cell 144. The laser source 146 of the probe 120 is operated with the beam directed to the measurement cell 144 that includes the reference gas 182, such that the beam interacts with the reference gas 182. A detector or detection arrangement 148 is provided for receiving at least one laser beam constituent subsequent to the interaction of the beam with the reference gas 182. Another step in the example method includes determining an accuracy and a calibration of the system from the at least one laser beam constituent of the reference gas 182.

The example of FIG. 3 and FIG. 4 shows an in-situ arrangement. In FIG. 3 and FIG. 4, the step of isolating the measurement cell 144 of the probe 120 includes moving the measurement cell 144 out of the exhaust passageway 112 and within a fixed shield 142 to isolate the measurement cell 144 from the exhaust gas wherein a seal 192 is provided at the end of the measurement cell 144. The seal 192 and the fixed shield 142 are configured to prevent exhaust gas 114 from entering the measurement cell 144 during the calibration of the system 110. The probe 120 can be moved manually or with the aid of various mechanical or electrically powered mechanisms. An aperture near the detection arrangement 148 penetrates though a wall 138 of the exhaust passageway 112 from the exterior of the passageway to the interior of the passageway. A sliding bar or other structure can be used to regulate communication between the interior of the probe 120 on the interior of the wall 138 and the exterior of the probe 120. The probe 120 has a guide path portion 140 that extends through the wall 138 and into the interior of the exhaust passageway 112. In FIG. 3, the probe 120 is in a position to measure and detect the pollution in the exhaust gas 114. When the user desires to calibrate the system, the user moves the probe 120, such as in a slidable movement within the fixed shield 142 or a sheath to the position of FIG. 4. In the position of FIG. 4, the measurement cell 144 is isolated from the exhaust gas 114. The reference gas source 180 can then be used to distribute or transport reference gas 182 into the probe 120 and into the measurement cell 144. The laser source 146 can then be activated to emit a laser beam to detect the reference gas 182. The seal 192 can further include a reflective surface 194 or other reflective device such that the detection arrangement 148 can receive information from the interaction of the laser with either the exhaust gas or the reference gas 182 and detect the varying energy levels of the laser as it interacts with either the exhaust gas 114 or the reference gas 182.

Figure 5:
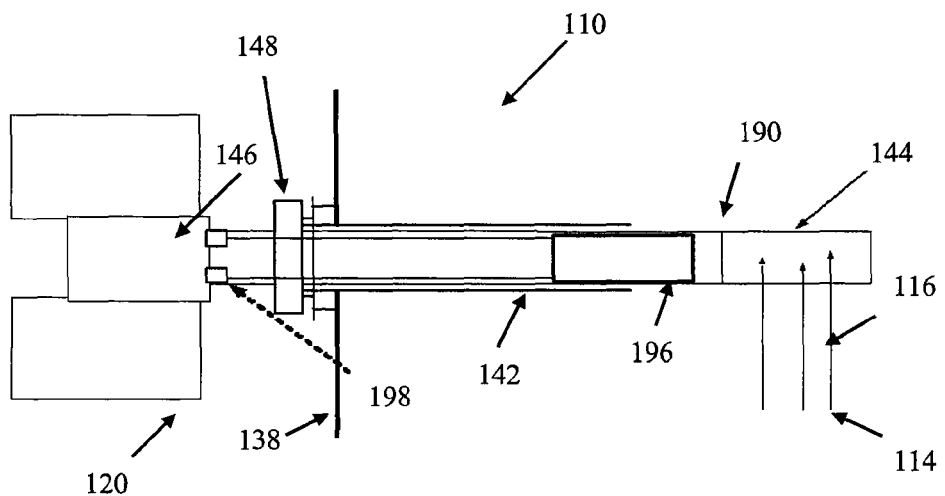
FIG. 5 is a schematic illustration of a system for measuring a pollution component of an exhaust gas and configured for conducting a calibration of the system where a probe includes an internal shield and where the internal shield is in a position that allows measuring and detecting of the pollution in the exhaust gas.
Figure 6:
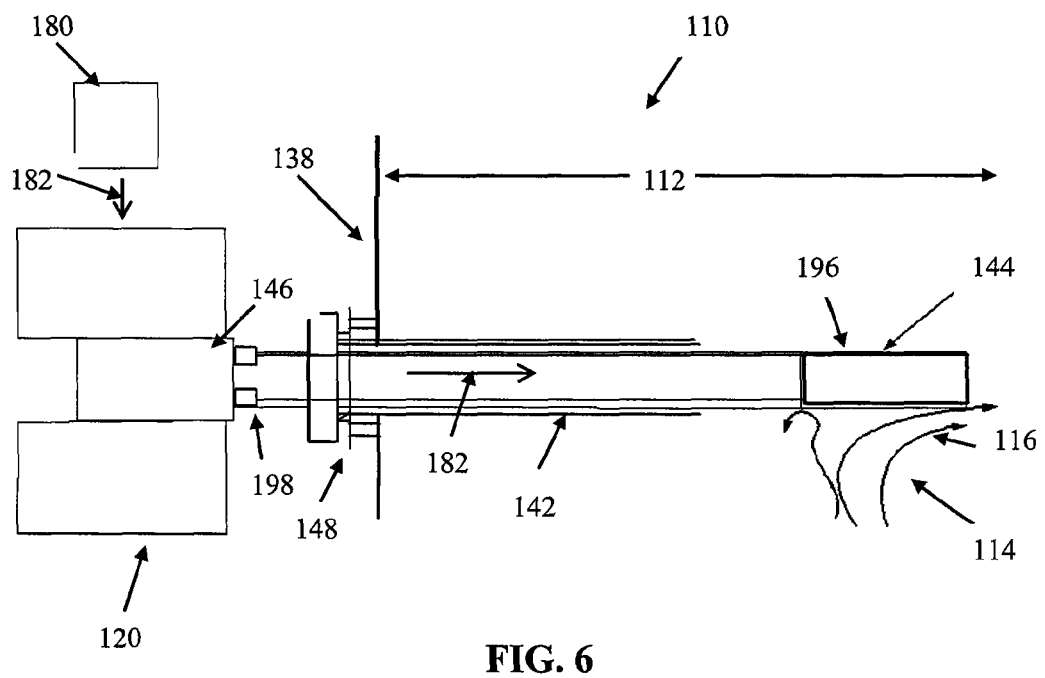
FIG. 6 is a schematic illustration of the system of FIG. 5 with the internal shield being placed in a position that isolates a measurement cell of the probe from the exhaust gas to allow calibration of the system to take place.

The example of FIG. 5 and FIG. 6 shows another in-situ arrangement of the first example system. In this example, an internal shield 196 is provided. The internal shield 196 is configured to be moved within the probe 120 either manually or through the aid of a power source 198. In the example shown, the power source can be a pneumatic or energized motor though other types of power sources can also be used. In the position of FIG. 5, the internal shield 196 is within the probe and does not interfere with the measurement cell 144 or the exhaust gas 114. In this position, the laser source 146 can be operated to measure the amount of pollution in the exhaust gas 114 as the exhaust gas 114 flows through the measurement cell 144. In the position of FIG. 6, the internal shield 196 is moved to a second position to isolate the measurement cell 144 from the exhaust gas 114. The internal shield 196 prevents the exhaust gas 114 from entering the measurement cell 144. By preventing the exhaust gas 114 from entering the measurement cell 144, a user can then distribute reference gas within the probe 120 which can reach the measurement cell 144. The detection arrangement 148 can then be used to calibrate the system 110 based off of the readings from a laser beam as it interacts with the reference gas 182.

The examples shown in FIGS. 3, 4, 5, and 6 can also include the hinge 49 shown in FIG. 2 and/or a screen 190. The hinge 49 can be positioned between the laser source 146 and the detection arrangement 148 to allow the removal of electronics and the maintenance of the probe 120 without the removal of other components. The screen 190 can be provided near the measurement cell 144 to limit particulate fouling.

Figure 7:
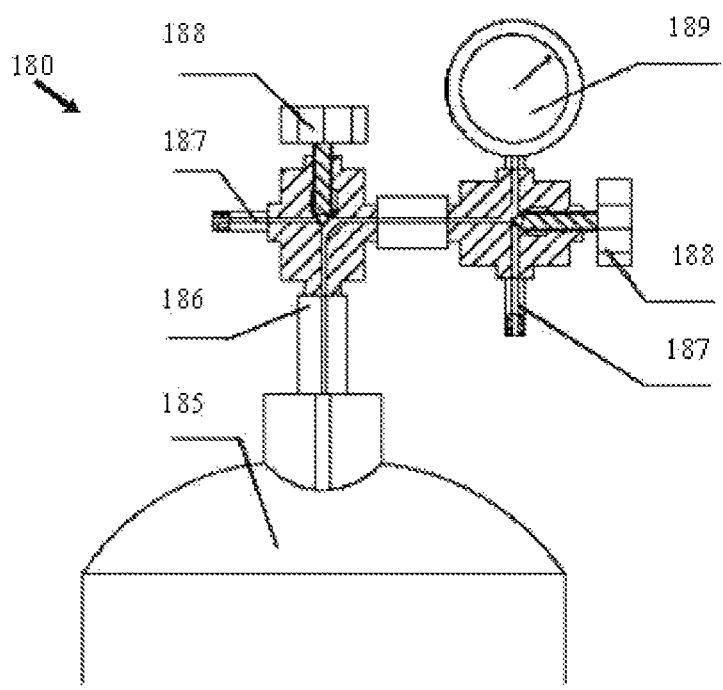
FIG. 7 is an illustration of an example reference gas source.

FIG. 7 shows an example of a reference gas source 180, which can be used as the reference gas source 180 in any of the examples. The reference gas source 180 can include a gas cylinder 185, a triple valve 186, a gas path 187, a knob 188, and a pressure measuring instrument 189 such as a manometer or pressure gauge. Many other examples can be provided to distribute reference gas to any of the systems in any of the examples.

Figure 8:
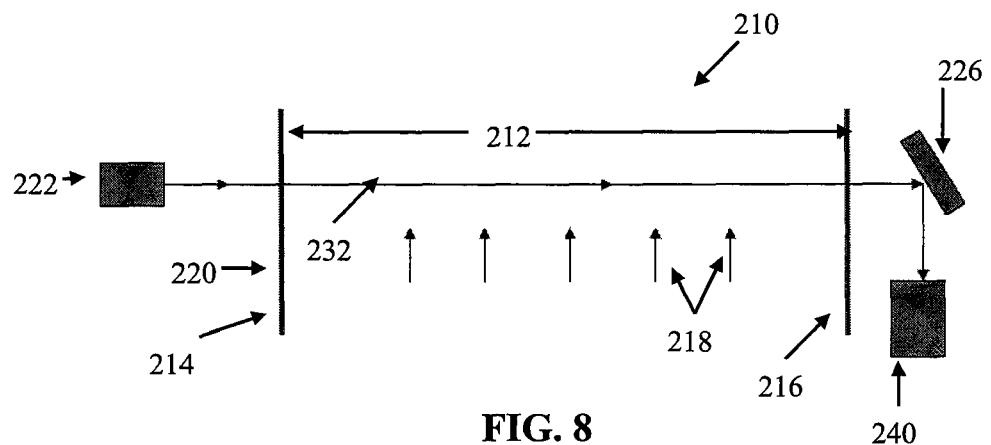
FIG. 8 is a schematic illustration of a system for measuring a pollution component of an exhaust gas across an exhaust passageway using a laser source on one side of the exhaust passageway and a detector on a second side of the exhaust passageway.
Figure 9:
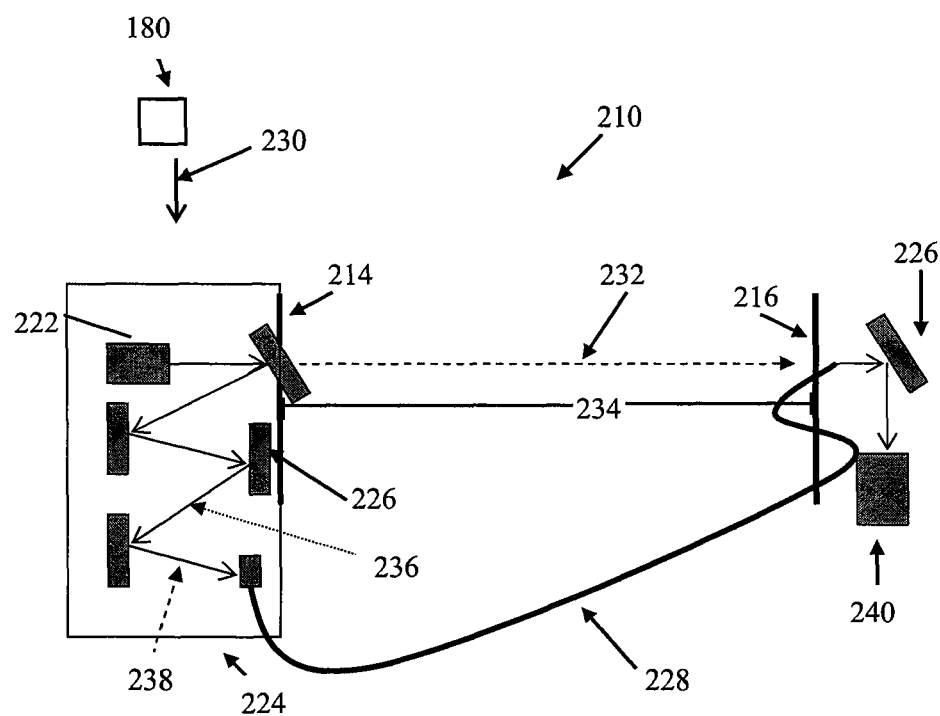
FIG. 9 is a schematic illustration of the system of FIG. 8 showing a calibration of the system where the detector receives a calibration measurement from a reference cell that detects reference gas.
Figure 10:
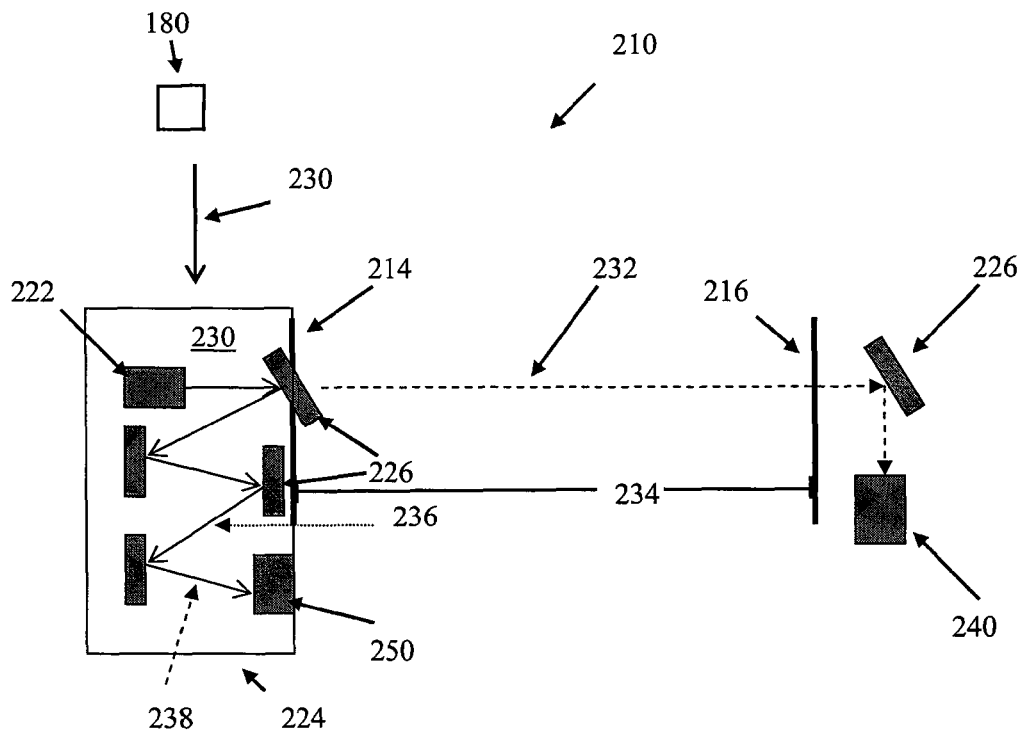
FIG. 10 is a schematic illustration of the system of FIG. 8 showing an alternative calibration of the system where the detector receives a calibration measurement from a second detector in a reference cell that detects reference gas.

FIGS. 8, 9, and 10 show a second example system 210 and method that is used to measure a pollution component of an exhaust gas within an exhaust passageway 212 and is also used for calibrating the system 210 without withdrawing gas from the system. The second example system 210 is able to detect pollution and allow calibration without withdrawing the exhaust gas 218 from the system as the measurements are performed cross-stack. This example system 210 includes providing a laser source 222 that emits a beam in the mid-infrared range from a first side 214 of the exhaust passageway 212 from a source stack 220. Cross-stack measurement of the exhaust gas 218 across an exhaust passageway 212 can then be performed. A detector 240 can be located about a second side 216 of the passageway 212 for receiving the beam during a measurement of the presence of the pollution component within the exhaust gas. The method further includes providing a closed coupled reference cell 224 on the first side 214 of the exhaust passageway 212 that is configured to be filled with reference gas during a calibration of the system. Another step in the method is to operate the laser source 222 to interact the beam of the laser with the reference gas during the calibration of the system. An accuracy and a calibration of the system from the at least one laser beam constituent of the reference gas.

The example of FIG. 8 shows how the measurement of the pollution component of a pollutant gas 218 is performed in the system 210. A measurement beam 232 from the laser source 222 is reflected off of a reflective device 226 in this example and to a first detector 240. The first detector measures the pollution component of the pollutant gas 218. The example of FIG. 8 and FIGS. 9 and 10 allows the system 210 to be used in a number of environments with varying distances for the exhaust passageway 212 due to the measurement and the calibration taking place across the stack or across the exhaust passageway 212.

FIG. 9 and FIG. 10 show examples of how a calibration of the system 210 is conducted. A source 180 of a reference gas 230 is provided and the reference gas 230 is transported to the closed coupled reference cell 224 when a calibration of the system is to be performed. The laser source 222 is operated to emit a beam to reflect off of a plurality of reflective devices 226. The closed coupled reference cell 224 can be designed such that a distance 234 of the passageway 212 between the first side 214 and the second side 216 is equal to a length 238 that the laser beam travels within the closed coupled reference cell 224 that reflects off of the number of reflective devices 226. For example, if a different sized exhaust passageway 212 is used, either a different number of reflective devices 226 can be used or the path of the reference beam 236 can be altered such that the length of the passageway 212 selected substantially corresponds to the length 238 of the path of the reference beam 236. Matching the length of the passageway 212 with the length that the laser beam travels in the closed coupled reference cell 224 provides an improved and more accurate calibration as the laser beam has to travel the same amount of distance in both a measurement operation and a calibration operation.

The example of FIG. 9 shows one example way of calibrating the system 210 shown in FIG. 8. In this example, the system 210 is calibrated with only a first detector 240. The first detector 240 that is used for measuring the presence of pollution, as shown in FIG. 8, receives at least one laser beam constituent subsequent to the interaction of the beam with the reference gas 230 in FIG. 9 through at least one connection 228 that is a cable, a fiber optic cable, or a wireless communication from the closed coupled reference cell 224. This example provides a benefit of the same detector being used for both calibration and measurement of the pollution of a pollutant gas. Providing the same detector can reduce the amount of error in the system to provide a more accurate calibration.

The example of FIG. 10 is another example way of calibrating the system 210 shown in FIG. 8. In this example, the system 210 is calibrated by providing a second detector 250 within the closed coupled reference cell 224. The second detector 250 receives at least one laser beam constituent subsequent to the interaction of the beam with the reference gas 230 during the calibration of the system. The laser beam received at the second detector 250 is compared during calibration with the laser beam received at the first detector 240, as shown in FIG. 8, during measurement of the exhaust gas 218. In either the example of FIG. 9 or the example of FIG. 10, the closed coupled reference cell 224 can be designed such that a distance of the passageway 212 between the first side 214 and the second side 216 is substantially equal to a length or distance 234 that the laser beam travels within the closed coupled reference cell 224 that reflects off of the number of reflective devices 226.

Figure 11:
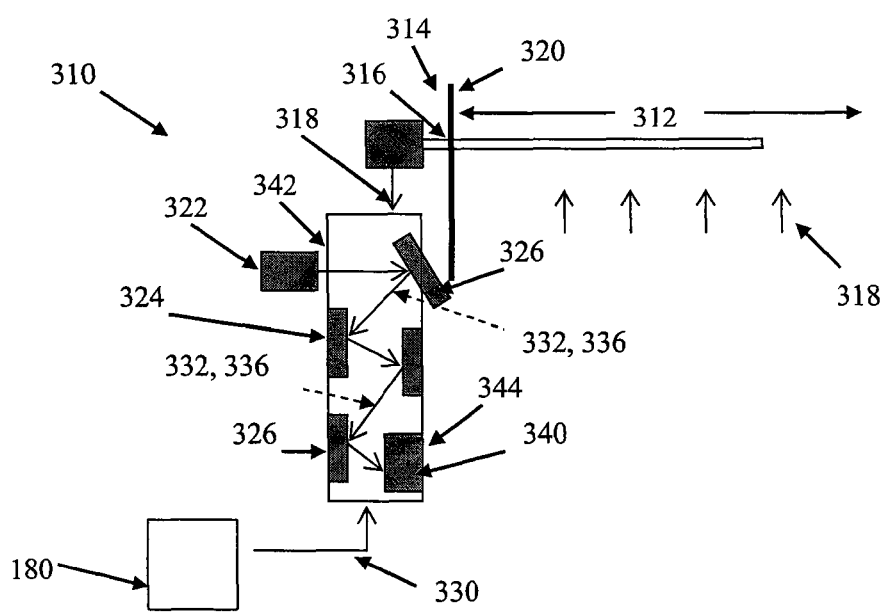
FIG. 11 is a schematic illustration of a system for measuring a pollution component of an exhaust gas across an exhaust passageway that extracts exhaust gas on one side of the exhaust passageway and uses a reference cell for detecting the pollution in the exhaust gas and for calibrating the system where reference gas can be transported to the reference cell.

The third example of FIG. 11 includes a method of calibrating a system 310 that detects a presence of a pollution component within an exhaust gas 318 within an exhaust passageway 312. The exhaust passageway 312 includes an exhaust extraction portion 316 in this example, which can be located on a first side 314 of the passageway 312. An aperture penetrates through a wall 320 of the exhaust passageway 312 from the exterior of the passageway to the interior of the passageway. A sliding bar or other structure can be used to regulate communication between the interior of the extractive portion 316 of the interior of the wall 320. The method includes the step of transporting the exhaust gas 318 from the exhaust extraction portion 316 to a closed coupled reference cell 324. Another step in the method includes providing a laser source 322 that emits a beam in the mid-infrared range from a first portion 342 of the closed coupled reference cell 324 for measuring the presence of the pollution component within the exhaust gas 318. Another step in the method includes providing a detector 340 on a second portion 344 of the closed coupled reference cell 324. The same closed coupled reference cell 324 can be filled with reference gas 330 when the user decides to calibrate the system 310. The laser source 322 is activated to interact with the reference gas 330. The detector 340 within the closed coupled reference cell 324 receives at least one laser beam constituent subsequent to the interaction of the beam with the reference gas 330. Accuracy and calibration of the system 310 are determined from the at least one laser beam constituent of the reference gas 330.

The third example system 310 can also include a measurement beam 332 from the laser source 322 that is reflected off of a reflective device 326 and to a first detector 340. The first detector 340 measures the pollution component of the pollutant gas 318. A reference beam 336 can be reflected off of a plurality of reflective devices 326 within the closed coupled reference cell 324. The laser source 322 is operated to emit a beam that can reflect off of the plurality of reflective devices 326.

In addition, various additional structures, functions, features and the like could be provided to each of the examples. Any of the examples can be utilized with the components of FIG. 1. For example, any of the systems 110, 210, 310 can include various components from the arrangement of FIG. 1 such as a hinge 49, a probe temperature controller 52, an analytical system 54, or a gas verification unit 60. In addition, various portions of any of the systems, such as the probe controller 22, could have a local display. Such a display could have use for functions such as calibration or direct reading. As another example, various portions of the system 10, such as the probe controller 22 or the programmable logic controller 26, could have data handling, recording, and reporting (e.g., via NetDAHS) functions. As still another example, it is possible to have optional data recording or reporting remotely (e.g., via an internet connection). In another example, the detection arrangement 48, 148 or the first detector 240, 340 can include a microprocessor to eliminate the need for an external computer. The probe and other components are designed to withstand the velocity of the exhaust gas which can be approximately 80 feet/second. The probe 20, 120 in any of the examples can also have an outer diameter of less than 3 inches in order to fit inside existing ports. Thus, the examples shown can be used to retrofit existing systems. The probe 20, 120 can also include extra holes/bulkheads to allow for the addition of feeding tubes through the flange to the optics area of the probe 20, 120 where air blowback might be required.

The invention has been described with reference to the example embodiments described above. Modifications and alterations will occur to others upon a reading and understanding of this specification. For example, Multi-component monitoring can be accomplished with one stack mounted probe using a single stack penetration and probe optics. Examples embodiments incorporating one or more aspects of the invention are intended to include all such modifications and alterations insofar as they come within the scope of the appended claims.

The invention claimed is:

1. A method of calibrating a system that detects a presence of a pollution component within an exhaust gas within an exhaust passageway, the method including:
    providing a probe with a measurement cell for in-situ measurement of the exhaust gas wherein the probe operates to detect the pollution component from the exhaust gas, the probe including a guide path portion that travels through a fixed shield, a laser that emits a beam in the mid-infrared range and is located on one end of the guide path portion, said measurement cell on an opposite end of the guide path portion, and a seal at an end of the measurement cell, the fixed shield being located within the exhaust passageway, and the measurement cell being able to be exposed to the exhaust gas within the exhaust passageway;
    moving the measurement cell out of the exhaust passageway and within the fixed shield to isolate the measurement cell from the exhaust gas, wherein the seal and the fixed shield are configured to prevent the exhaust gas from entering the measurement cell during the calibration of the system;
    providing a source of a reference gas that is transported to the measurement cell; operating the laser of the probe with the beam directed to the measurement cell that includes the reference gas, such that the beam interacts with the reference gas;
    receiving at a detector the laser beam subsequent to the interaction of the beam with the reference gas; and
    determining an accuracy and a calibration of the system from the at least one or more constituents of the reference gas.

2. The method of claim 1, wherein the probe includes hinge to allow the removal of electronics and maintenance of the probe without the removal of other components.

3. The method of claim 1, wherein the probe includes a screen near the measurement cell to limit particulate fouling.

4. The method of claim 1, further including determining a value indicative of a concentration of the pollution component within the exhaust gas.

5. The method of claim 1, wherein the step of providing the probe includes operating the laser in a frequency range of 4000 to 650 $em^{-1}$.

6. The method of claim 1, wherein the step of providing the probe includes providing the laser that is a quantum cascade laser.

7. The method of claim 1, wherein the step of providing the probe includes providing the probe without external cooling.

8. The method of claim 1, wherein the step of operating the laser of the probe includes operating the laser in a pulsed or continuous operation mode.

* * * * *